US012606786B2

(12) United States Patent
Merz et al.

(10) Patent No.: US 12,606,786 B2
(45) Date of Patent: Apr. 21, 2026

(54) METHOD AND SYSTEM FOR AN AUTOMATED MICROBIAL MONITORING PROCESS IN AN ISOLATOR

(71) Applicant: Groninger & Co. GmbH, Crailsheim (DE)

(72) Inventors: Armin Merz, Ellwangen (DE); Roland Engelhard, Aurach-Weinberg (DE)

(73) Assignee: GRONINGER & CO. GMBH, Crailsheim (DE)

( * ) Notice: Subject to any disclaimer, the term of this patent is extended or adjusted under 35 U.S.C. 154(b) by 801 days.

(21) Appl. No.: 17/878,996

(22) Filed: Aug. 2, 2022

(65) Prior Publication Data

US 2022/0380710 A1     Dec. 1, 2022

Related U.S. Application Data

(63) Continuation of application No. PCT/EP2021/052446, filed on Feb. 2, 2021.

(30) Foreign Application Priority Data

Feb. 4, 2020     (DE) ..................... 10 2020 102 758.3

(51) Int. Cl.
*C12M 1/00*          (2006.01)
*B25J 11/00*         (2006.01)
(Continued)

(52) U.S. Cl.
CPC .............. *C12M 23/50* (2013.01); *B25J 11/00* (2013.01); *B25J 21/005* (2013.01); *C12M 23/38* (2013.01); *C12M 41/14* (2013.01); *C12M 41/48* (2013.01)

(58) Field of Classification Search
CPC ...... C12M 23/50; C12M 23/38; C12M 41/14; C12M 41/48; C12M 37/06; B25J 11/00; B25J 21/005; C12Q 1/22; A61L 2/28
See application file for complete search history.

(56) References Cited

U.S. PATENT DOCUMENTS 5,730,777 A * 3/1998 Petersen .................. B25J 21/02
                                                        55/467
2004/0185521 A1* 9/2004 Yoshida ................. B25J 21/005
                                                        435/287.9
(Continued)

FOREIGN PATENT DOCUMENTS

DE       102009039547 A1     3/2011
DE       102015210842 B3    12/2016
JP        2017113836 A       6/2017

OTHER PUBLICATIONS

Examination Report issued by the German Patent Office for application DE 10 2020 102 758.3 on Dec. 7, 2020; 4 pages.
(Continued)

*Primary Examiner* — Michael L Hobbs
(74) *Attorney, Agent, or Firm* — Reising Ethington P.C.

(57) ABSTRACT

A method for automated microbial monitoring in an isolator having a transfer lock, the method comprising the steps: first providing at least one nutrient medium carrier holder at, in each case, a first position within the isolator; second providing at least one nutrient medium carrier within the transfer lock; first robot-assisted transferring of an individual nutrient medium carrier from the transfer lock to a free nutrient medium carrier holder; and first robot-assisted placing of the transferred nutrient medium carrier in the free nutrient medium carrier holder. Further, a system for automated microbial monitoring in an isolator and a computer program are also disclosed.

21 Claims, 14 Drawing Sheets

(51) Int. Cl.
  B25J 21/00          (2006.01)
  C12M 1/36          (2006.01)

(56)                    References Cited

U.S. PATENT DOCUMENTS

2004/0215362 A1 *  10/2004  Kokubo ................. C12M 41/14
                                                                  700/130
2005/0042710 A1    2/2005  Oshima
2014/0377038 A1   12/2014  Malin
2018/0133893 A1    5/2018  Motojima et al.

OTHER PUBLICATIONS

English translation of the examination report issued by the German
Patent Office for application DE 10 2020 102 758.3 on Dec. 7, 2020;
4 pages.
English translation of the International Preliminary Report on
Patentability issued for PCT/EP2021/052446 on Jul. 28, 2022; 6
pages.
International Search Report and Written Opinion issued for PCT/
EP2021/052446 on May 28, 2021.
Office Action issued by the Canadian Patent Office for application
CA 3,166,086 on Jul. 9, 2025.

* cited by examiner

METHOD AND SYSTEM FOR AN AUTOMATED MICROBIAL MONITORING PROCESS IN AN ISOLATOR

CROSS-REFERENCE TO RELATED APPLICATIONS

This is a Continuation application of International patent application PCT/EP2021/052446, filed Feb. 2, 2021, which claims the priority of German patent application DE 10 2020 102 758.3, filed Feb. 4, 2020. Both application PCT/EP2021/052446 and DE 10 2020 102 758.3 are herewith incorporated by reference in their entirety.

BACKGROUND

The present application relates to a method, a system and a computer program for automated microbial monitoring in an isolator.

The present application is primarily concerned with aseptic isolators, which for example have a filling region for filling objects (e. g. vials, carpules, bottles, syringes and/or the like) with fluid by means of filling needles. The term "isolator" is generally understood to mean a container which is sealed hermetically and in a gas-tight manner from the surrounding working space. A defined atmosphere for processing sensitive or hazardous products can be generated within an isolator.

In this context, isolators are usually used in biopharmaceutical process technology, for example as part of a filling system with several process and processing stations, to create a highly pure or sterile, i.e. aseptic, environment and to avoid contamination by microbes, in particular bacteria, viruses, pathogens and/or the like.

Pharmaceutical filling systems are usually in a sterile environment. A sterile environment must be present in the filling region within the isolator. This state is monitored by placing microbe collectors at the critical locations. Microbe collectors can, for example, be Petri dishes that have a nutrient medium. If a microbe gets onto the nutrient medium, the microbe grows during the subsequent incubation, which means that contamination can be detected retrospectively. Such monitoring of a sterile environment is called "microbial monitoring" or "microbiological monitoring".

Various methods and systems have been proposed in the prior art for microbial monitoring of an isolator. On the one hand, microbe collectors, used in passive microbial monitoring, are positioned inside the isolator such that ambient air flows past them. Microbes that are present in the air flowing past are able to settle on the nutrient medium. Before the start of production, these microbe collectors are introduced into the isolator and positioned inside the isolator in a sterile manner via transfer locks, for example alpha-beta ports, using gloves. The Petri dishes can additionally have a lid, which is likewise removed using gloves.

Since the nutrient media dry out over time, they are usually replaced after a maximum of four hours. To do this, production has to be interrupted. By further intervention using gloves, the lid is placed back onto the previously used Petri dish, and the Petri dish is transferred back to the port. From the outside, the Petri dish is then removed from the port and transported in a sterile state into an incubator. Before the start of production again, a new Petri dish with nutrient medium is inserted using gloves and the lid is removed.

On the other hand, in active microbial monitoring, the microbe collectors are inserted into a housing and arranged within the isolator. The housings actively suck in air, which then flows past the microbe collectors. The housing has a lid. In active microbial monitoring, the introduction and removal of microbe collectors takes place using gloves in the same way as in passive microbial monitoring. In addition, in the case of active microbial monitoring, the lid of the housing has to be removed before the microbe collectors can be inserted into the housing.

However, this "manual" handling by way of gloves is extremely time-consuming. Furthermore, glove ducts, which in practice are made of rubber or plastic, in particular butyl, may become damaged when gripping the Petri dishes or the lids. The use of gloves therefore also poses an increased risk of contamination and/or an increased safety risk as a result of leaks. In addition, manual glove interventions can lead to microbes located on the nutrient medium being carried over.

In the prior art, it is generally known that objects, for example Petri dishes, can be handled within an isolator by means of robots.

For example, the document JP 2017 113836 A discloses a hand for a cell culture vessel, which hand can be mounted on a tip of a multi-joint robot in order to handle a cell culture vessel having a lid. The hand comprises a hand stem, a container-holding part on a lower side for releasably holding the cell culture vessel, and a lid-holding part on an upper side for releasably holding the lid. In the hand for a cell culture vessel, the vessel-holding part and the lid-holding part are attached to the hand stem in such a way that they approach each other and can be separated vertically.

Furthermore, the document DE 10 2015 210 842 B3 discloses a device for gripping, singulating, transporting and/or depositing Petri dishes and a method for operating the device. The device has a moving unit which is controlled by an electronic control unit, connected to it, and which has at least one degree of freedom. A gripper is arranged on/in the moving unit and has two horizontally oriented frame elements which at least partially engage about the circumference of Petri dishes of different diameters and which are connected to a drive, the latter being connected to the electronic control unit such that the frame elements are movable horizontally toward each other and away from each other. The distance between the frame elements is adjustable via the electronic control unit. On each frame element, a gripping element for gripping and holding Petri dishes is arranged between the gripping elements of the two frame elements, the gripping elements being mounted so as to be vertically movable and able to return to an original position by way of springs attached to the frame elements and gripping elements. Arranged on at least one gripping element is a component which moves together with the gripping element, and the position of the component is detected with an associated sensor for detecting the component, which sensor is arranged on a frame element and connected to the electronic control unit. Also arranged on each frame element are extensible units which are connected to the electronic control unit and controlled by it, and which move an ejector plate vertically downward by means of lifting magnets, with springs for returning to an original position, and the ejector plates, when gripping a Petri dish, bear on the bottom of the respective Petri dish.

The known systems and methods for microbial monitoring still leave room for improvements in terms of handling and operational safety.

3
SUMMARY

Against this background, it is an object of the present application to make available an improved method, an improved system and a computer program that permits better handling and operational safety.

According to a first aspect, a method for automated microbial monitoring in an isolator is provided. The isolator has a transfer lock. The method comprises the following steps:

first providing of at least one nutrient medium carrier holder at in each case a first position within the isolator;

second providing of at least one nutrient medium carrier within the transfer lock;

first robot-assisted transferring of an individual nutrient medium carrier of the at least one nutrient medium carrier from the transfer lock to a free nutrient medium carrier holder of the at least one nutrient medium carrier holder; and first robot-assisted placing of the transferred nutrient medium carrier in the free nutrient medium carrier holder.

According to a second aspect, a system for automated microbial monitoring in an isolator is provided. The system has the isolator, at least one nutrient medium carrier holder, a robot arranged in the isolator, and a control device, wherein the isolator has a transfer lock, wherein at least one nutrient medium carrier is provided in the transfer lock, wherein the nutrient medium carrier holder is arranged at a first position within the isolator, wherein the robot has an end effector for handling a nutrient medium carrier and a support structure for supporting the end effector, wherein the support structure is configured to move the end effector in the isolator, wherein the end effector is configured to grip the nutrient medium carrier, and wherein the control device is configured to carry out the following steps:

first robot-assisted transferring of in each case an individual nutrient medium carrier of the at least one nutrient medium carrier from the transfer lock to a free nutrient medium carrier holder of the at least one nutrient medium carrier holder; and first robot-assisted placing of the transferred nutrient medium carrier in the free nutrient medium carrier holder.

According to a third aspect, a computer program with a program code is provided which is configured, when executed in the control device of the system according to the second aspect, to carry out the following steps:

first robot-assisted transferring of an individual nutrient medium carrier of the at least one nutrient medium carrier from the transfer lock to a free nutrient medium carrier holder of the at least one nutrient medium carrier holder; and first robot-assisted placing of the transferred nutrient medium carrier in the free nutrient medium carrier holder.

The isolator is preferably an aseptic isolator. An aseptic isolator has a highly pure or sterile, i.e. microbe-free, environment. The isolator has a transfer lock. In the present case, such a transfer lock can be, for example, a flexible sterile bag via which the articles arrangeable in the sterile bag (e.g. filling needles, needle carriers, objects, etc.) are fed, in a pre-sterilized state, through a lock system or closure system to the aseptic isolator, preferably for filling the objects. Such sterile bags are known in isolator technology. They generally have an adapter with which the sterile bag can be coupled in a sterile manner, for example, to a so-called alpha port of the aseptic isolator. An alpha port can be a recess, e.g. a through-hole and/or a door or the like, in a wall portion of the aseptic isolator. The sterile bag can have a beta port, which can be configured for example as a door or the like, which is attached to the alpha port in such a way that the alpha port and the beta port can be opened together.

Alternatively, however, the transfer lock can also be configured as a rigid transport container which can be coupled to the alpha port of the aseptic isolator according to the aforementioned principle, in order to permit sterile transfer of the articles arrangeable therein into the aseptic isolator.

The term "nutrient medium carrier" is to be understood here as a device which is configured to carry a nutrient medium. A nutrient medium carrier can be, for example, a Petri dish or an agar plate in which the nutrient medium is arranged.

The term "nutrient medium carrier holder" is to be understood here as a device on which a nutrient medium carrier can be placed or set down. For this purpose, the nutrient medium carrier holder can have a support surface on which the nutrient medium carrier can be placed or set down. Alternatively, the nutrient medium carrier holder can also have a receptacle into which the nutrient medium carrier can be inserted.

The term "robot-assisted" is to be understood as meaning that something is carried out with the aid of a robot. For example, "robot-assisted transferring of a nutrient medium carrier" means that the nutrient medium carrier is transferred with the aid of the robot. For this purpose, the robot can, for example, have a movable support structure, at the end of which an end effector is mounted, the end effector being able to grip the nutrient medium carrier for transfer.

As was mentioned at the outset, the term "isolator" is to be understood here as a container which is sealed hermetically and in a gas-tight manner from the surrounding working space. The term isolator chamber can also be used for the isolator. A defined atmosphere for processing sensitive or hazardous products, in particular pharmaceutical or cosmetic products, can be generated within the isolator. The isolator can be an aseptic isolator. An aseptic isolator can be, for example, a clean room, an ultraclean room or the like.

Furthermore, the term "transfer lock" here denotes a device for the transition between two regions with preferably different properties, in particular a region within the aseptic isolator and a region outside the aseptic isolator. In the context of the present application, the transfer lock is preferably configured in such a way that an aseptic state is provided within the transfer lock or can optionally be produced. It can thereby be ensured that the articles to be transferred do not impair or destroy the existing aseptic state within the aseptic isolator. Such methods for producing an aseptic environment within the transfer lock are known in the industry.

The term "robot-assisted" or "robot" is to be understood here as meaning that the identified method steps are carried out by means of an automated movement apparatus of any kind. This can be, for example, a handling unit, a manipulator, a kinematics system or the like that forms the robot. A "robot" signifies a movement apparatus having at least one support structure, in particular an articulated support structure, at the end of which a robot end effector is arranged. The support structure is configured to move the robot end effector in all three spatial directions.

The movement apparatus can be, for example, a construction with multi-axis movements of any kind. For example, such a construction can have two to six axis movements of any kind.

For the first robot-assisted transferring, the nutrient medium carrier to be transferred can be arranged in or at the transfer lock. "At the transfer lock" is to be understood as meaning that the nutrient medium carrier extends at least partially out of the transfer lock into the isolator. In other words, the nutrient medium carrier can be arranged at least partially or completely within the isolator, in particular adjoining the transfer lock or adjacent to the transfer lock. In the step of robot-assisted transferring of the nutrient medium carrier from the transfer lock to the free nutrient medium carrier holder, the nutrient medium carrier is thus transferred, with robot assistance, from its arrangement in or at the transfer lock to the free nutrient medium carrier holder.

Automated microbial monitoring is made possible by the robot-assisted transferring of a nutrient medium carrier from the transfer lock to a nutrient medium carrier holder within the isolator and by the robot-assisted placing of the nutrient medium carrier on the nutrient medium carrier holder. This improves the handling and operational safety during the microbial monitoring.

In a first refinement, the method comprises, before the step of first robot-assisted transferring, the following step:

first robot-assisted removing of the nutrient medium carrier, which is to be transferred, from the transfer lock.

"Robot-assisted removing of a nutrient medium carrier" means that the nutrient medium carrier is removed from the transfer lock by means of a robot. For example, the robot can grip the nutrient medium carrier in order to remove it. In this way, the nutrient medium carrier can be introduced into the isolator in a simple manner.

In a further refinement, each nutrient medium carrier has a dish with nutrient medium and a lid which is placed on an opening of the dish, the method further comprising the following steps:

third providing of at least one lid holder for storing the lid of the transferred nutrient medium carrier, the at least one lid holder being provided at in each case a second position within the isolator.

The term "lid holder" is to be understood here as a device on which a lid of a nutrient medium carrier can be deposited. For this purpose, the lid holder can have a support surface on which the lid can be deposited. Alternatively, the lid holder can also have a receptacle into which the lid can be inserted. In this way, even if the nutrient medium carrier has a lid, it is made possible that the automated microbial monitoring can be carried out in the isolator by means of a robot. Without a lid holder, the lid would have to be held by the robot throughout the microbial monitoring process, up to the point in time when the lid can be put back on, the robot therefore being unable to perform any further operations during this time.

In a further refinement, the method further comprises the following steps:

robot-assisted removing of the lid from the dish of the transferred nutrient medium carrier;

second robot-assisted transferring of the lid from the nutrient medium carrier holder to a free lid holder of the at least one lid holder; and robot-assisted depositing of the lid on the free lid holder.

"Robot-assisted removing of a lid" is understood to mean that the lid is removed from the nutrient medium carrier by means of a robot. To remove it, the robot can, for example, grip and lift the lid. "Robot-assisted depositing of a lid" is understood to mean that the lid is deposited on the lid holder by means of a robot. To deposit it, the robot can, for example, set the lid down on the lid holder and release it. In this way, the lid can be removed as easily as possible from the nutrient medium carrier without the use of gloves. In addition, this also allows the automated microbial monitoring to be carried out in the isolator by means of a robot.

In a further refinement, the method further comprises the following steps, after the transferred nutrient medium carrier has spent a predefined period of time in the corresponding nutrient medium carrier holder:

robot-assisted removing of the lid from the lid holder;

third robot-assisted transferring of the lid from the lid holder to the corresponding nutrient medium carrier holder; and robot-assisted fitting of the lid onto the dish of the nutrient medium carrier.

"Robot-assisted removing of a lid" is understood to mean that the lid is removed from the lid holder by means of a robot. For this removal, the robot can, for example, grip and lift the lid. "Robot-assisted fitting of a lid" is understood to mean that the lid is fitted on the dish of the nutrient medium carrier by means of a robot. The robot can, for example, fit the lid on the dish and release it. In this way, the lid can be fitted onto the nutrient medium carrier as easily as possible without use of gloves.

In a further refinement, the method further comprises the following steps, after the transferred nutrient medium carrier has spent a predefined period of time in the corresponding nutrient medium carrier holder:

second robot-assisted removing of the nutrient medium carrier from the nutrient medium carrier holder;

fourth robot-assisted transferring of the nutrient medium carrier from the nutrient medium carrier holder to the transfer lock; and second robot-assisted placing of the nutrient medium carrier in the transfer lock.

In this way, the nutrient medium carrier can be removed from the isolator through the transfer lock as easily as possible without use of gloves, in order to then place the nutrient medium carrier in an incubator. The predefined period of time can be four hours, for example.

In a further refinement, in the step of the first providing, a microbial monitoring device with at least one nutrient medium carrier holder is provided.

The microbial monitoring device can be used, for example, for active microbial monitoring, with ambient air being actively sucked in so as to allow it to flow past a nutrient medium carrier arranged in the nutrient medium carrier holder. In this way, active microbial monitoring can also be operated in an automated manner.

In a further refinement, the microbial monitoring device has a housing in which the at least one nutrient medium carrier holder is arranged, the housing having a housing lid, wherein the method further comprises the following steps:

fourth providing of a housing lid holder within the isolator at a third position;

robot-assisted removing of the housing lid; and robot-assisted depositing of the housing lid on the housing lid holder.

The term "housing lid holder" is to be understood here as a device on which the housing lid can be deposited. For this purpose, the housing lid holder can have a support surface on which the housing lid can be deposited. Alternatively, the housing lid holder can also have a receptacle into which the housing lid can be inserted. In this way, it is made possible that the automated microbial monitoring can be carried out in the isolator by means of only one robot.

In a further refinement, in the step of the second providing, a plurality of nutrient medium carriers are provided in the transfer lock, wherein, in the step of the third providing, a storage device with a plurality of holders is provided at the second position, which holders are each able to serve as nutrient medium carrier holder or lid holder.

In this way, the plurality of nutrient medium carriers can be stored in the storage device. The holders serve as nutrient medium carrier holders. For microbial monitoring, one nutrient medium carrier can then always be removed from the store and inserted into the nutrient medium carrier holder of the microbial monitoring device. A holder in the storage device thus becomes free, in which holder the lid of the nutrient medium carrier inserted into the nutrient medium carrier holder of the microbial monitoring device can then be placed. This holder then serves as a lid holder. In this way, the number of insertion and removal processes through the transfer lock can be reduced, thereby reducing the risk of contamination.

In a further refinement, in the step of the first providing, the plurality of nutrient medium carriers are provided in a nutrient medium carrier retainer in the transfer lock.

The nutrient medium carrier retainer can have a plurality of nutrient medium carrier holders for the nutrient medium carriers. In this way, a plurality of nutrient medium carriers can be provided in the transfer lock as simply as possible and in as orderly a manner as possible. This also improves the removal of the individual nutrient medium carriers from the transfer lock. After the predefined period of time, the nutrient medium carriers can be put back into the nutrient medium carrier retainer. In this way, a plurality of nutrient medium carriers can be inserted and removed at the same time, which means that the replacement of nutrient media can take place more quickly and more efficiently.

In a further refinement, in the step of the second providing, each nutrient medium carrier is provided in a further nutrient medium carrier holder, wherein each further nutrient medium carrier holder is arranged in the transfer lock, in particular wherein the nutrient medium carrier retainer has each further nutrient medium carrier holder.

In this way too, each nutrient medium carrier can be provided in the transfer lock as simply as possible and in as orderly a manner as possible. This also improves the removal of each individual nutrient medium carrier from the transfer lock. After the predefined period of time, each nutrient medium carrier can be put back into the corresponding nutrient medium carrier holder.

In a further refinement, each further nutrient medium carrier holder can extend at least partially out of the transfer lock into the isolator, in particular wherein the step of the first robot-assisted transferring from the transfer lock to the free nutrient medium carrier holder takes place in such a way that the respective further nutrient medium carrier holder extends at least partially out of the transfer lock into the isolator and the corresponding nutrient medium carrier is transferred, with robot assistance, from the respective further nutrient medium carrier holder to the free nutrient medium carrier holder within the isolator.

in this way, each nutrient medium carrier can be removed better and more easily from the corresponding further nutrient medium carrier holder, in order for it then to be transferred, with robot assistance, to the free nutrient medium carrier holder within the isolator.

In a further refinement, a robot is arranged in the isolator, wherein the robot has an end effector for handling a nutrient medium carrier and a support structure for supporting the end effector, wherein the support structure is configured to move the end effector in the isolator, wherein the end effector is configured to grip the nutrient medium carrier.

The end effector can furthermore be configured to grip the lid of the nutrient medium carrier. The end effector can furthermore be configured to grip the housing lid of the housing. The support structure can, for example, be configured to be articulated, in particular multi-articulated, the support structure being moved by means of one or more drive devices. The end effector can be mounted rotatably at one end of the support structure. In this way, the nutrient medium carrier or the lid or the housing lid can be easily transferred with the aid of the robot in the isolator.

In a further refinement, the number of nutrient medium carriers provided in the transfer lock is one, two, three, four, five, six, seven, eight, nine, ten, eleven or twelve.

With one to four nutrient medium carriers, the automated microbial monitoring can be operated in an isolator in an efficient manner.

In a further refinement, the number of nutrient medium carrier holders provided in the isolator is equal to or greater than the number of nutrient medium carriers provided in the transfer lock.

In this way, it is made possible that a free nutrient medium carrier holder is present for each nutrient medium carrier that is introduced into the transfer lock.

In a further refinement, the number of lid holders provided in the isolator is equal to or greater than the number of nutrient medium carriers provided in the transfer lock.

It is in this way made possible that, for each nutrient medium carrier that is introduced into the transfer lock, a free lid holder is present on which the lid of the nutrient medium carrier can be deposited. The nutrient medium carriers can be brought to the monitoring position gradually. In this case, only one lid holder is ever in use. Just a single lid holder can then be necessary and present. However, a plurality of monitoring positions can also be operated from a pool. More lid holders are then needed.

In a further refinement, the number of holders of the storage device is equal to or greater than the number of nutrient medium carriers provided in the transfer lock.

It is in this way made possible that sufficient nutrient medium carrier holders and lid holders are available whenever an opened nutrient medium carrier is arranged in the nutrient medium carrier holder of the microbial monitoring device.

In a further refinement, the end effector has a receptacle for receiving the nutrient medium carrier, which receptacle is movable between a receiving position, in which the nutrient medium carrier can be received, and a gripping position, in which the nutrient medium carrier can be gripped, in particular wherein each nutrient medium carrier for transferring can be gripped by means of the end effector and moved by means of the robot within the isolator.

In other words, for gripping purposes, the end effector has a receptacle which is movable between a receiving position and a gripping position. In the receiving position, the receptacle is opened so wide that the nutrient medium carrier or the lid or the housing lid can be inserted into the receptacle. In the gripping position, the receptacle is closed so far that the nutrient medium carrier or the lid or the housing lid is gripped. In this way, the nutrient medium carrier or the lid or the housing lid can be easily transferred with the aid of the robot in the isolator.

In a further refinement, the system has a microbial monitoring device with at least one nutrient medium carrier holder.

The microbial monitoring device can be used, for example, for active microbial monitoring, with ambient air being actively sucked in so as to allow it to flow past a nutrient medium carrier arranged in the nutrient medium carrier holder. In this way, active microbial monitoring can also be operated in an automated manner.

In a further refinement, the microbial monitoring device has a housing in which at least one nutrient medium carrier holder is arranged, wherein the housing has a housing lid, wherein the housing lid is removable by means of the robot, wherein the system has a housing lid holder for storing the housing lid, wherein the housing lid holder is arranged at a third position within the isolator.

For this purpose, the housing lid holder can have a support surface on which the housing lid can be deposited. Alternatively, the housing lid holder can also have a receptacle into which the housing lid can be inserted. In this way, it is made possible that the automated microbial monitoring can be carried out in the isolator by means of only one robot.

In a further refinement, each nutrient medium carrier has a dish with nutrient medium and a lid which is placed on an opening of the dish, wherein the lid can be removed by means of the robot, wherein the system furthermore has at least one lid holder for storing the lid, wherein the at least one lid holder is arranged inside the isolator at a second position in each case.

A lid holder allows the automated microbial monitoring in the isolator to be carried out by means of one robot, even if the nutrient medium carrier has a lid. In particular, the system can have a lid holder device with a plurality of lid holders. In this way, a plurality of lids can be deposited on the respective lid holders as simply as possible and in as orderly a manner as possible. This allows the lids to be stored during the microbial monitoring.

In a further refinement, the system also has a storage device with a plurality of holders, the storage device being arranged at the second position, the holders each being able to serve as nutrient medium carrier holders or lid holders.

In this way, the plurality of nutrient medium carriers can be stored in the storage device. The holders serve as nutrient medium carrier holders. For microbial monitoring, one nutrient medium carrier can then always be removed from the store and inserted into the nutrient medium carrier holder of the microbial monitoring device. A holder in the storage device thus becomes free, in which holder the lid of the nutrient medium carrier inserted into the nutrient medium carrier holder of the microbial monitoring device can then be placed. This holder then serves as a lid holder. In this way, the number of insertion and removal processes through the transfer lock can be reduced, thereby reducing the risk of contamination.

It will be appreciated that the aforementioned features and the features still to be explained below can be used not only in the respectively cited combination, but also in other combinations or singly, without departing from the scope of the present invention.

BRIEF DESCRIPTION OF THE SEVERAL VIEWS OF THE DRAWING

Embodiments of the application are explained in more detail in the following description and are shown in the drawing, in which.

DETAILED DESCRIPTION

Figure 1:
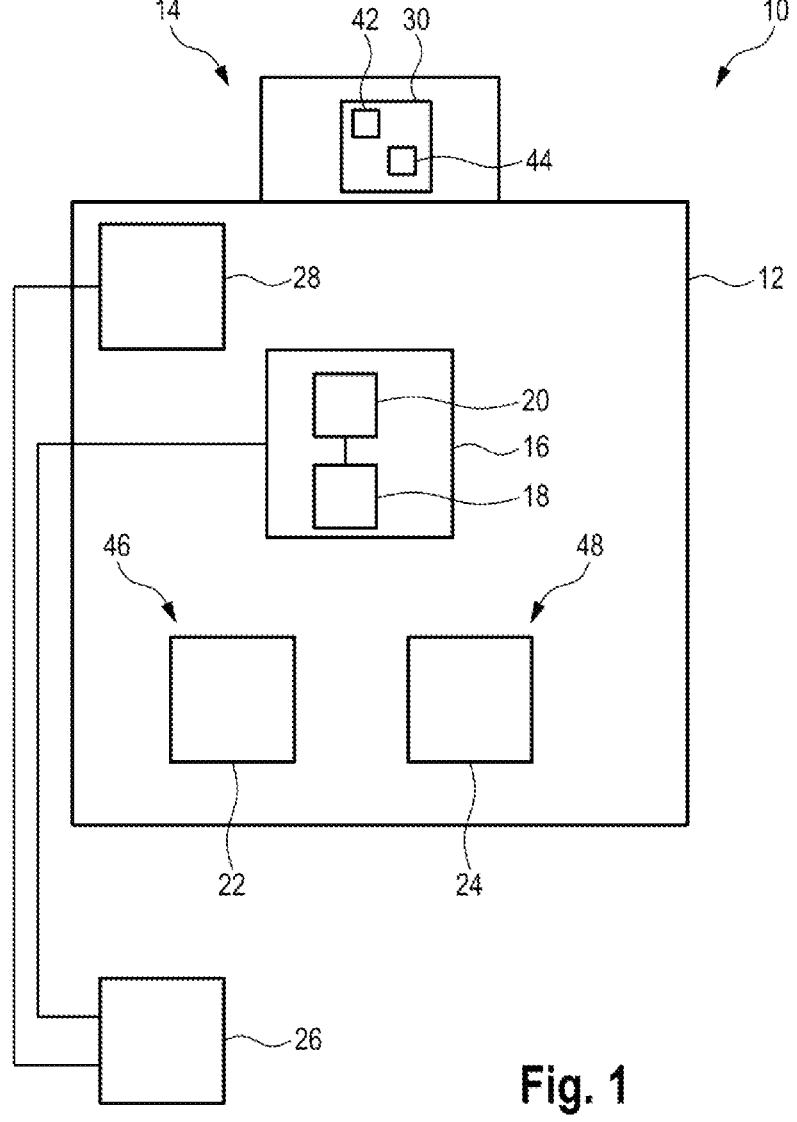
FIG. 1 shows a schematic representation of a first embodiment of a system for automated microbial monitoring in an isolator.

FIG. 1 shows a first embodiment of a system 10 for automated microbial monitoring in an isolator 12. The system 10 has the isolator 12. The isolator 12 has a transfer lock 14. The transfer lock 14 adjoins the isolator 12. A nutrient medium carrier 30 can be provided in the transfer lock 14. The nutrient medium carrier 30 has a dish 42 with nutrient medium and a lid 44. The lid 44 can be placed onto the dish 42 in order to close the dish, or can be removed from the dish 42 in order to open the dish 42. In the opened state, ambient air comes into contact with the nutrient medium. It is also possible for a plurality of nutrient medium carriers 30 to be provided in the transfer lock 14. For example, in the transfer lock 14, a nutrient medium carrier retainer can be provided which has a plurality of nutrient medium carrier holders in which the nutrient medium carriers 30 of the plurality of nutrient medium carriers are arranged.

The system 10 moreover has a robot 16. The robot 16 is arranged in the isolator 12. The robot 16 has a support structure 18 and an end effector 20. The end effector 20 is configured to handle a nutrient medium carrier. In particular, the end effector 20 is configured to grip the nutrient medium carrier 30. The support structure 18 is configured to support the end effector 20. In particular, the support structure 18 is configured to move the end effector 20 in the isolator 12. For this purpose, the support structure 18 can be configured, for example, to be articulated, in particular multi-articulated. Furthermore, the end effector 20 can be arranged at one end of the support structure 18 and, in particular, can be rotatably mounted. The robot 16 can furthermore have one or more drive devices which are configured to move the support structure 18 and to rotate the end effector 20 at the end of the support structure 18, as a result of which the end effector 20 can be moved and oriented in the isolator.

The end effector 20 can, for example, have a receptacle for receiving the nutrient medium carrier 30. The receptacle can be movable between a receiving position, in which the nutrient medium carrier 30 or the lid 44 can be received, and a gripping position, in which the nutrient medium carrier 30 or the lid 44 can be gripped. In order to move the receptacle between the receiving position and the gripping position, the end effector 20 can have a drive device. For the transfer, the nutrient medium carrier 30 can be gripped by means of the end effector 20 and can be moved in the isolator by means of the robot 16.

The system 10 furthermore has a nutrient medium carrier holder 22. The nutrient medium carrier holder 22 is provided at a first position 46 within isolator 12. The nutrient medium carrier holder 22 is configured in such a way that a nutrient medium carrier, for example the nutrient medium carrier 30, can be deposited or set down on the nutrient medium carrier holder 22. For this purpose, the nutrient medium carrier holder 22 can, for example, have a support surface on which the nutrient medium carrier 30 can be deposited or set down. The system can have a plurality of nutrient medium carrier holders 22 which are each provided at, in particular different, first positions 46 within the isolator 12. The number of nutrient medium carrier holders 22 is preferably equal to or greater than the number of nutrient medium carriers 30 provided.

The system 10 furthermore has a lid holder 24. The lid holder 24 is provided at a second position 48 within isolator 12. The lid holder 24 is configured in such a way that a lid of a nutrient medium carrier, for example the lid 44 of the nutrient medium carrier 30, can be deposited on the lid holder 24. For this purpose, the lid holder 24 can, for example, have a support surface on which the lid 44 of the nutrient medium carrier 30 can be deposited. The system can have a plurality of lid holders 24 which are each provided at, in particular different, second positions 48 within the isolator 12. The number of lid holders 24 is preferably equal to or greater than the number of nutrient medium carriers 30 provided.

The system 10 furthermore has a control device 26. The control device 26 is configured to control the robot 16. The control device 26 can control the robot in such a way that the end effector 20 is moved and oriented in the isolator 12 and that nutrient medium holders and lids can be removed or picked up and deposited or set down by means of the end effector. For this purpose, the control device 26 can send control signals to the robot 16, for example. In particular, the control device 26 can send control signals to the drive devices of the robot 16 in order to move and orient the end effector in space. Furthermore, the control device 26 can send control signals to the drive device of the end effector in order to move the receptacle of the end effector 20 between the receiving position and the gripping position.

The system 10 can furthermore have a sensor device 28. The sensor device 28 is configured to determine the position and orientation of the end effector and of the object to be transferred, for example the nutrient medium carrier 30 or the lid 44. For this purpose, the sensor device 28 can have optical sensors, for example. The sensor device 28 can be configured to send sensor signals to the control device 26. The sensor signals can, for example, contain information concerning the position and orientation of the end effector and of the object to be transferred. The control device 26 can furthermore be configured to control the robot 16 on the basis of the received sensor signals.

Figure 2A:
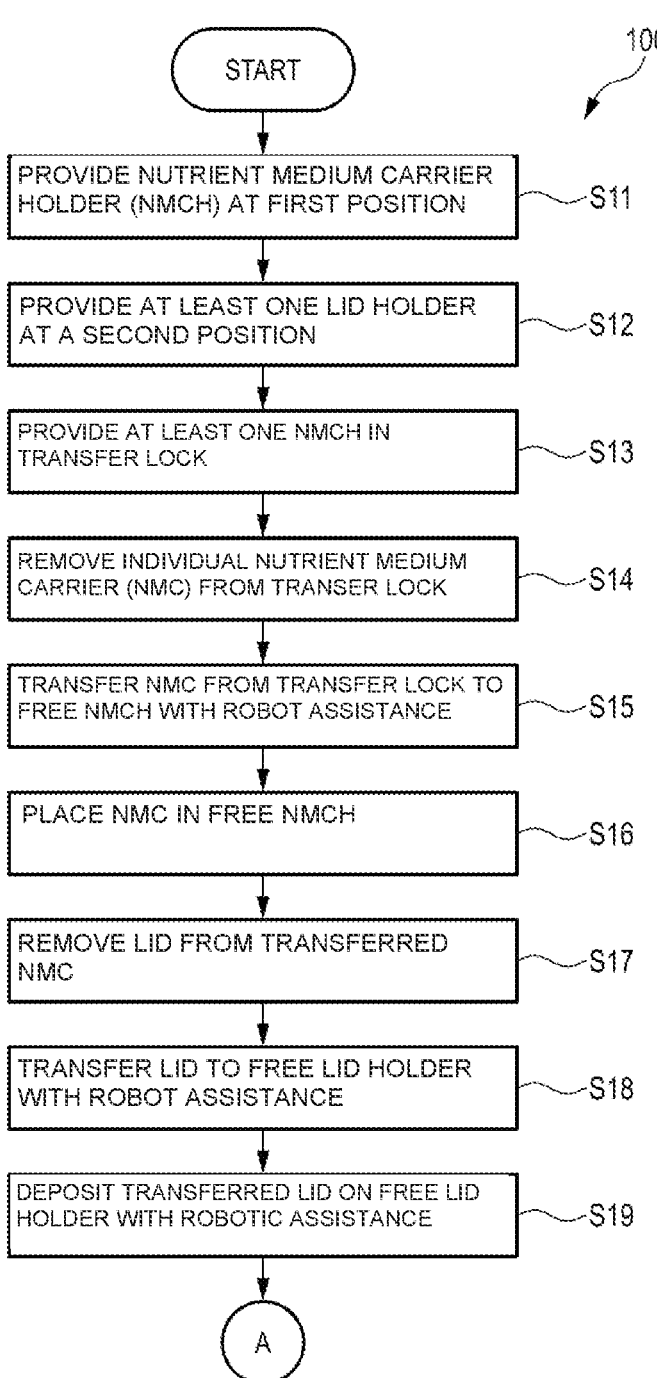
FIGS. 2A, 2B show a schematic representation of a first embodiment of a method for automated microbial monitoring in an isolator.
Figure 2B:
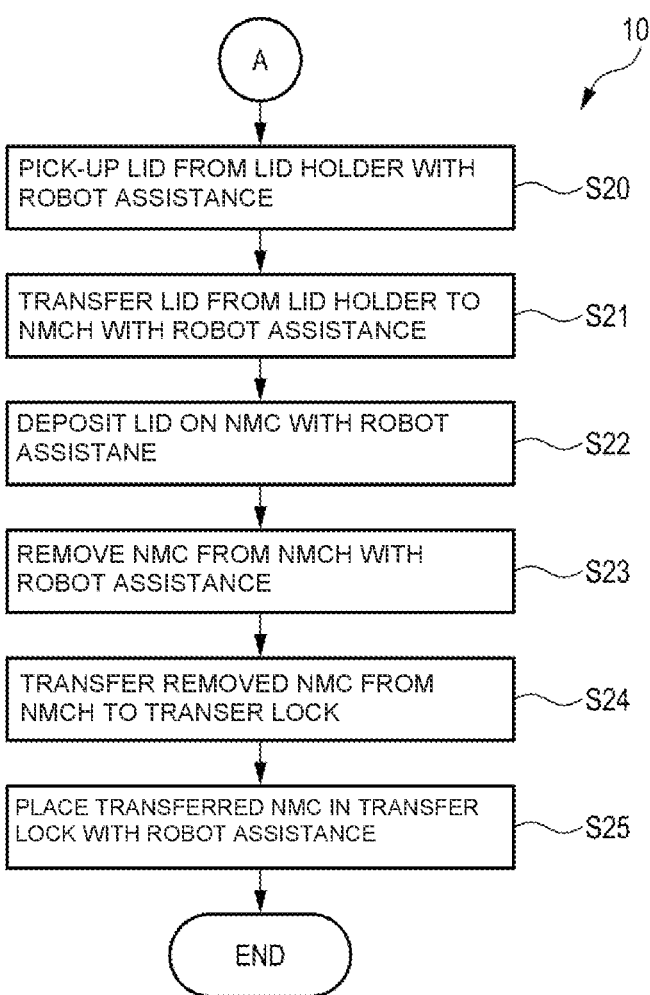

FIG. 2 shows a first embodiment of a method 100 for automated microbial monitoring in an isolator 12. The method can be carried out, for example, by means of the system 10 from FIG. 1. In particular, the control device 26 can be configured to carry out steps S14 to S25.

In a first step S11 of the method 100, at least one nutrient medium carrier holder 22 is provided at a first position 46 within the isolator 12.

In a further step S12 of the method 100, at least one lid holder 24, for storing the lid 44 of a nutrient medium carrier 30 that is to be transferred, is provided at a second position 48 within the isolator 12.

Steps S11 to S12 can be carried out in any desired sequence.

In a further step S13 of the method 100, at least one nutrient medium carrier 30 is provided within the transfer lock 14.

In a further step S14 of the method 100, an individual nutrient medium carrier 30 of the at least one nutrient medium carrier 30 is removed from the transfer lock 14 with robot assistance. For this purpose, the robot 16 can be controlled, for example, in such a way that the end effector 20 is moved to the nutrient medium carrier 30 that is to be transferred, and the end effector 20 grips the nutrient medium carrier 30 that is to be transferred.

In a further step S15 of the method 100, the removed nutrient medium carrier 30 is transferred, with robot assistance, from the transfer lock 14 to a free nutrient medium carrier holder 22 of the at least one nutrient medium carrier holder 22. For this purpose, for example, the robot 16 can be controlled, for example, in such a way that the end effector 20 is moved from the transfer lock 14 to the free nutrient medium carrier holder 22.

In a further step S16 of the method 100, the transferred nutrient medium carrier 30 is placed in the free nutrient medium carrier holder 22 with robot assistance. The nutrient medium carrier 30 is set down in particular on a support surface of the nutrient medium carrier holder 22. For this purpose, the robot can be controlled, for example, in such a way that the end effector 20 places the nutrient medium carrier 30, which is to be transferred, on the support surface and releases it.

In a further step S17 of the method 100, the lid 44 of the transferred nutrient medium carrier 30 is removed from the dish 42 with robot assistance. For this purpose, the robot 16 can be controlled, for example, in such a way that the end effector 18 grips the lid 44 and lifts it.

In a further step S18 of the method 100, the lid 44 is transferred, with robot assistance, from the nutrient medium carrier holder 22 to a free lid holder 24 of the at least one lid holder 24. For this purpose, the robot 16 can be controlled, for example, in such a way that the end effector 18 moves the gripped lid 44 from the nutrient medium carrier holder 22 to the free lid holder 24.

In a further step S19 of the method 100, the transferred lid 44 is deposited with robot assistance on the free lid holder 24. For this purpose, the robot 16 can be controlled, for example, in such a way that the end effector 18 deposits the transferred lid 44 on the lid holder 24, in particular sets it down and releases it.

If a plurality of nutrient medium carriers 30 are provided in the transfer lock 14, steps S14 to S19 can be repeated for each nutrient medium carrier 30.

Each dish 42 of the at least one nutrient medium carrier 30 then remains for a predefined period of time in the respective nutrient medium carrier holder 22 in the opened state, as a result of which microbial monitoring is carried out in this period of time. The predefined period of time can be 4 hours, for example.

In a further step S20 of the method 100, after the transferred nutrient medium carrier 30 has spent the predefined period of time in the corresponding nutrient medium carrier holder 22, the lid 44 of the nutrient medium carrier 30 is picked up from the lid holder 24 with robot assistance. For this purpose, the robot 16 can be controlled, for example, in such a way that the end effector 18 grips the lid 44 and lifts it.

In a further step S21 of the method 100, the lid 44 is transferred with robot assistance from the lid holder 24 to the nutrient medium carrier holder 22 on which the dish 42 of the nutrient medium carrier 30 is arranged. For this purpose, the robot 16 can be controlled, for example, in such a way that the end effector 18 moves the gripped lid 44 from the lid holder 46 to the nutrient medium carrier holder 22.

In a further step S22 of the method 100, the lid 44 is deposited with robot assistance on the dish 42 of the nutrient medium carrier 30. For this purpose, the robot 16 can be controlled, for example, in such a way that the end effector 18 places the lid 44 on the dish 42 and releases it.

In a further step S23 of the method 100, the nutrient medium carrier 30 is removed from the nutrient medium carrier holder 22 with robot assistance. For this purpose, the robot 16 can be controlled, for example, in such a way that the end effector 18 grips the closed nutrient medium carrier 30.

In a further step S24 of the method 100, the removed nutrient medium carrier 30 is transferred, with robot assistance, from the nutrient medium carrier holder 22 to the transfer lock 14. For this purpose, the robot 16 can be controlled, for example, in such a way that the end effector 18 moves the nutrient medium carrier 30 from the nutrient medium carrier holder 22 to the transfer lock 14.

In a further step S25 of the method 100, the transferred nutrient medium carrier 30 is placed in the transfer lock 14 with robot assistance. For this purpose, the robot 16 can be controlled, for example, in such a way that the end effector 18 deposits the nutrient medium carrier 30 in the transfer lock 14 and releases it.

If a plurality of nutrient medium carriers 30 are used, steps S20 to S25 can be repeated for each nutrient medium carrier 30.

Figure 3:
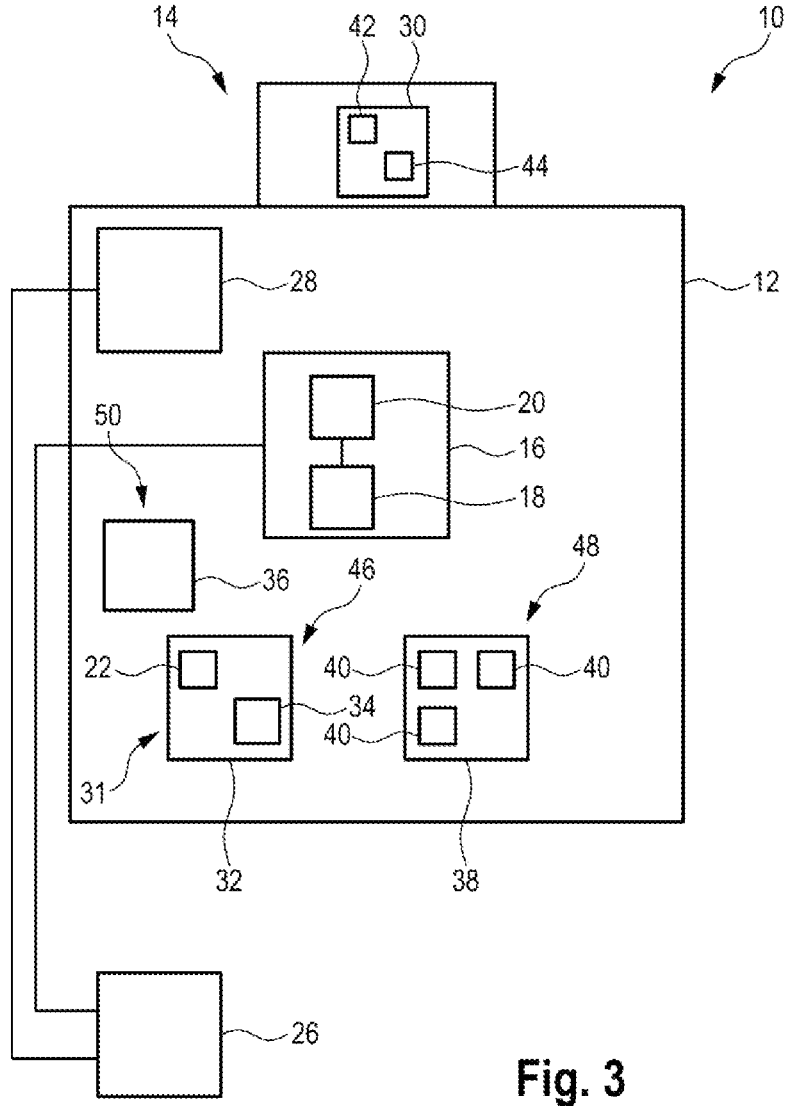
FIG. 3 shows a schematic representation of a second embodiment of a system for automated microbial monitoring in an isolator.
Figure 4:
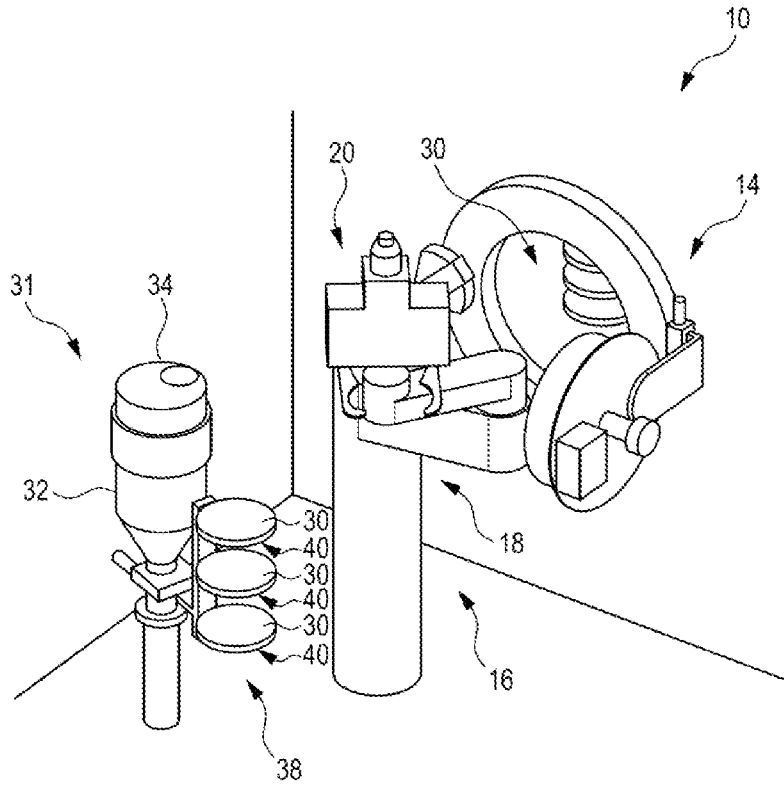
FIG. 4 shows an isometric view of the system of FIG. 3.

FIGS. 3 and 4 show a second embodiment of a system 10 for automated microbial monitoring in an isolator 12. The system 10 corresponds substantially to the system 10 of the first embodiment from FIG. 1. The same elements are identified by the same reference signs and are explained again.

The system 10 of the second embodiment also has a microbial monitoring device 31. The microbial monitoring device 31 has a housing 32 and a housing lid 34. The microbial monitoring device 31 has the nutrient medium carrier holder 22. The nutrient medium carrier holder 22 is arranged in the housing 32. It is also possible for a plurality of nutrient medium carrier holders 22 to be arranged in the housing 32.

The system 10 of the second embodiment also has a housing lid holder 36. The housing lid holder 36 is provided at a third position 50 within the isolator. The housing lid holder 36 is configured in such a way that the housing lid 34 can be deposited on the housing lid holder 36. For this purpose, the housing lid holder 36 can, for example, have a support surface on which the housing lid 34 can be deposited.

The system 10 of the second embodiment also has a storage device 38. The storage device 38 has at least one holder 40. Each holder 40 serves as a nutrient medium carrier holder or as a lid holder. In particular, each holder 40 is configured in such a way that both an entire nutrient medium carrier 30 and a lid 44 can be deposited on the holder 40. The storage device 38 can also have a plurality of holders 40. In particular, the storage device 38 can have three holders 40. The storage device 38 can be mounted on the microbial monitoring device 31. FIG. 4 also shows, by way of example, how three nutrient medium carriers 30 are arranged in the holders 40, the holders 40 serving as nutrient medium carrier holders.

Figure 5:
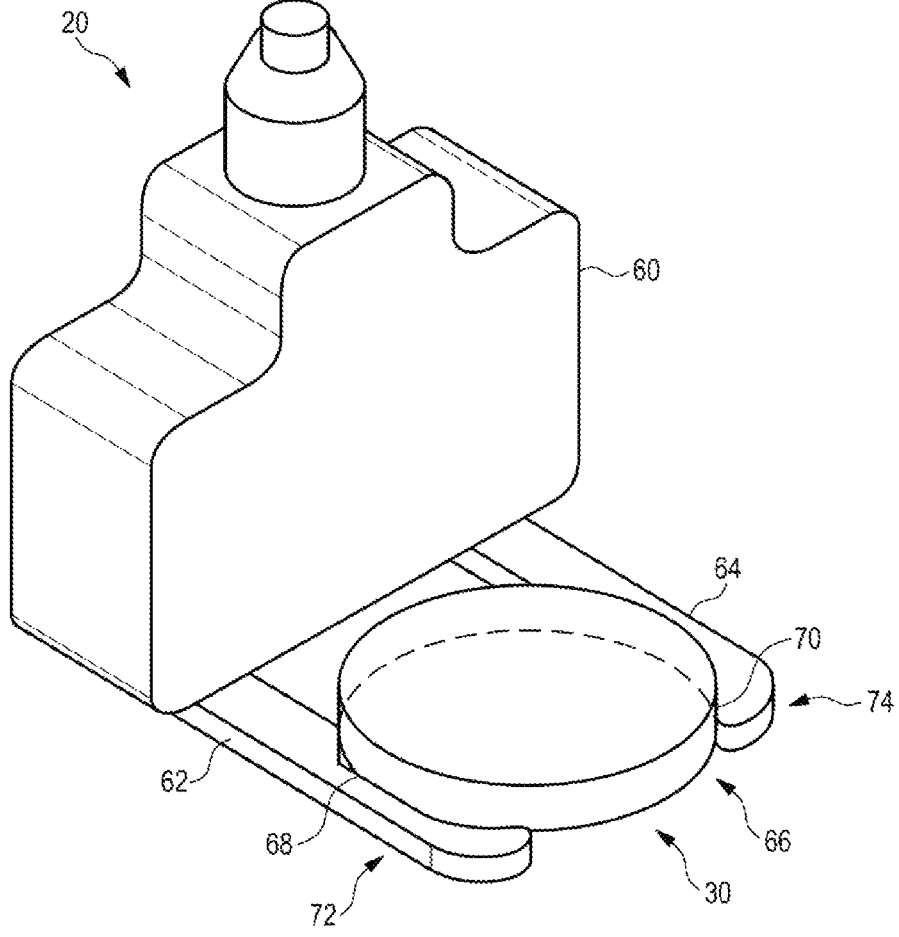
FIG. 5 shows an isometric view of an end effector with a nutrient medium carrier.

In FIG. 5, the end effector 20 of the robot 16 of the system 10 of the second embodiment is shown in detail.

The end effector 20 has a receptacle 66 for receiving a nutrient medium carrier 30 or a lid 44. The receptacle 66 can be moved between a receiving position, in which the nutrient medium carrier 30 or the lid 44 can be received, and a gripping position, in which the nutrient medium carrier 30 or the lid 44 can be gripped. For this purpose, the end effector 20 has a base body 60, a first displacement element 62 and a second displacement element 64. The first displacement element 62 and the second displacement element 64 are each mounted rotatably or displaceably on an underside of the base body 60. The displacement elements 62, 64 extend parallel to each other in a direction of extension away from the base body 60. At an end 72, 74 facing away from the base body, each displacement element 62, 64 has a respective gripping portion 68, 70. The receptacle 66 is arranged between the displacement elements 62, 64. The receptacle 66 has the gripping portions 68 and 70, the gripping portions 68, 70 being arranged on opposite sides of the receptacle 66.

In order to move the receptacle 66, the displacement elements 62, 64 are moved in such a way that the gripping portions are moved toward each other for displacement to the gripping position and are moved away from each other for displacement to the receiving position. For this purpose, the displacement elements 62, 64 can be movable either in rotation or in translation. In order to move the receptacle 66 between the receiving position and the gripping position, the end effector 20 can have a drive device which is configured to move the displacement elements 62, 64 accordingly in translation or rotation.

Figure 6:
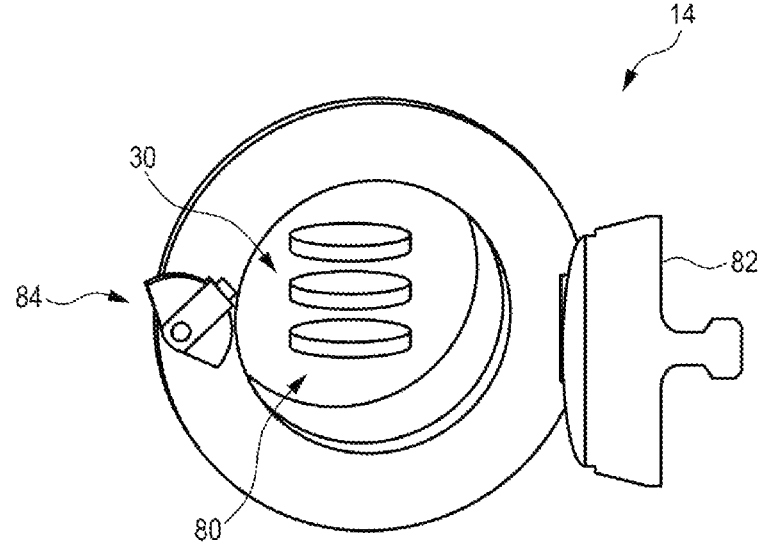
FIG. 6 shows an isometric view of a transfer lock with nutrient medium carriers arranged therein.

In FIG. 6, the transfer lock 14 of the isolator 12 of the system 10 of the second embodiment is shown in detail.

The transfer lock 14 has a lock interior 80 and a door 82. The nutrient medium carriers 30 can be provided in the lock interior. The door 82 is movable between an open position, in which the lock interior 80 is connected to the interior of the isolator 12, and a closed position, in which the lock interior 80 is separated from the interior of the isolator 12. The transfer lock 14 also has a latching element 84, by means of which the door can be locked in the closed position. The door is shown in the open position in FIG. 6.

Figure 7:
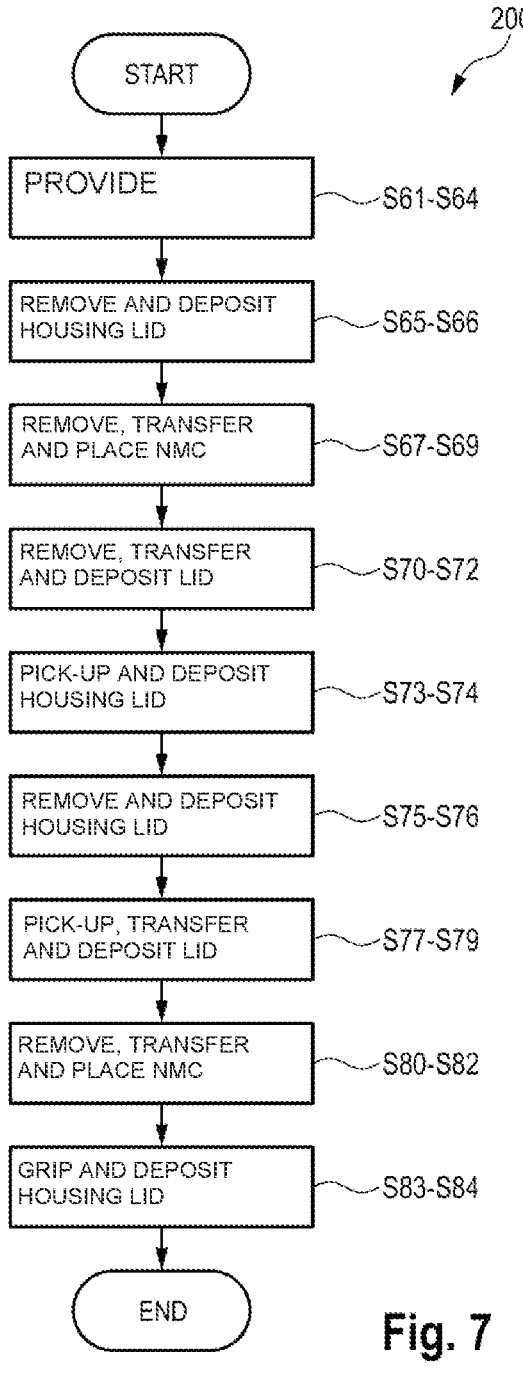
FIG. 7 shows a schematic representation of a second embodiment of a method for automated microbial monitoring in an isolator.

FIG. 7 shows a second embodiment of a method 200 for automated microbial monitoring in an isolator 12. The method can be carried out, for example, by means of the system 10 from FIGS. 3 and 4. In particular, the control device 26 can be configured to carry out steps S65 to S84.

In a first step S61 of the method 200, the microbial monitoring device 31 with at least one nutrient medium carrier holder 22 is provided at a first position 46 within the isolator 12.

In a further step S62 of the method 200, the storage device 38 with at least one holder 40 is provided at a second position 48 within the isolator 12, the holder 40 serving as a lid holder 24 on which the lid 44 of a transferred nutrient medium carrier 30 is deposited.

In a further step S63 of the method 200, a housing lid holder 36 for storing the housing lid 34 is provided at a third position 50 within the isolator 12.

Steps S61 to S63 can be carried out in any desired sequence.

In a further step S64 of the method 200, at least one nutrient medium carrier 30 is provided within the transfer lock 14.

Figures 8A, 8B:
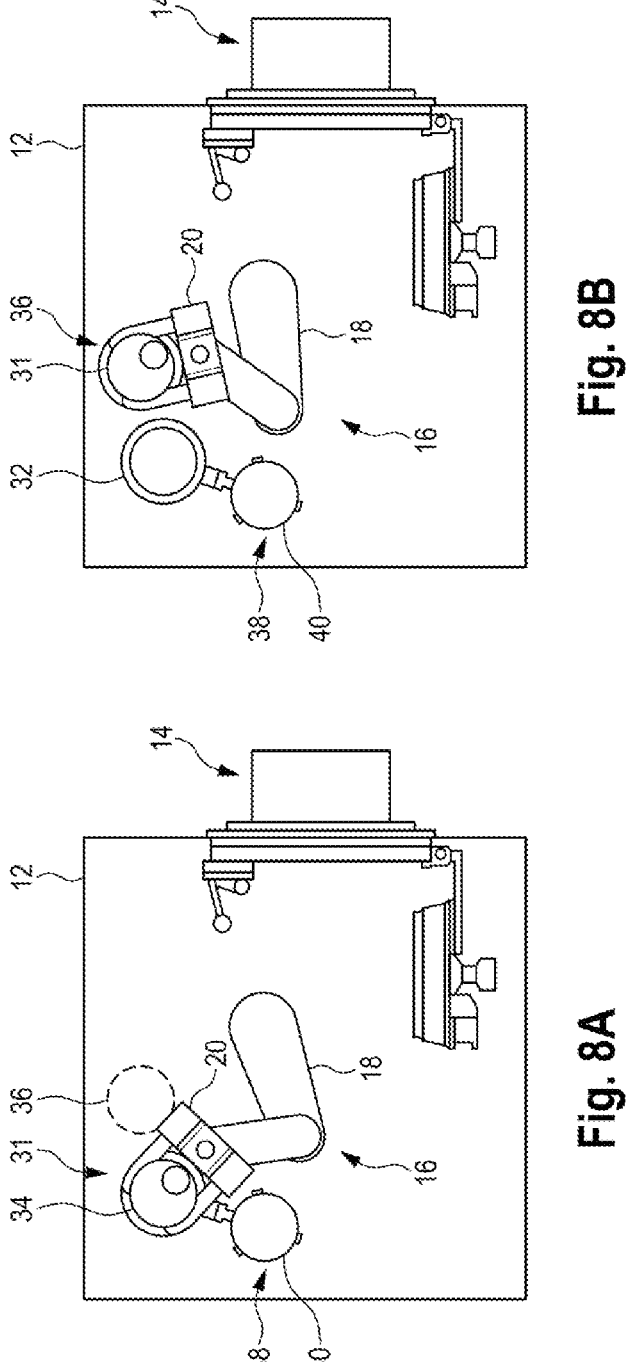
FIG. 8A shows a plan view of the system from FIG. 4 when the housing lid is removed from the housing of the microbial monitoring device.
FIG. 8B shows a plan view of the system from FIG. 4 when the housing lid is deposited on the housing lid holder.

In a further step S65 of the method 200, the housing lid 34 is removed, with robot assistance, from the housing 32 of the microbial monitoring device 31. For this purpose, the robot 16 can be controlled, for example, in such a way that the end effector 18 grips the housing lid 34 and lifts it. This is shown by way of example in FIG. 8A.

In a further step S66 of the method 200, the housing lid 34 is deposited on the housing lid holder 36 with robot assistance. For this purpose, the robot 16 can be controlled, for example, in such a way that the end effector 18 deposits the housing lid 34 on the housing lid holder 36, in particular sets it down and releases it. This is shown by way of example in FIG. 8B.

Figures 9A, 9B:
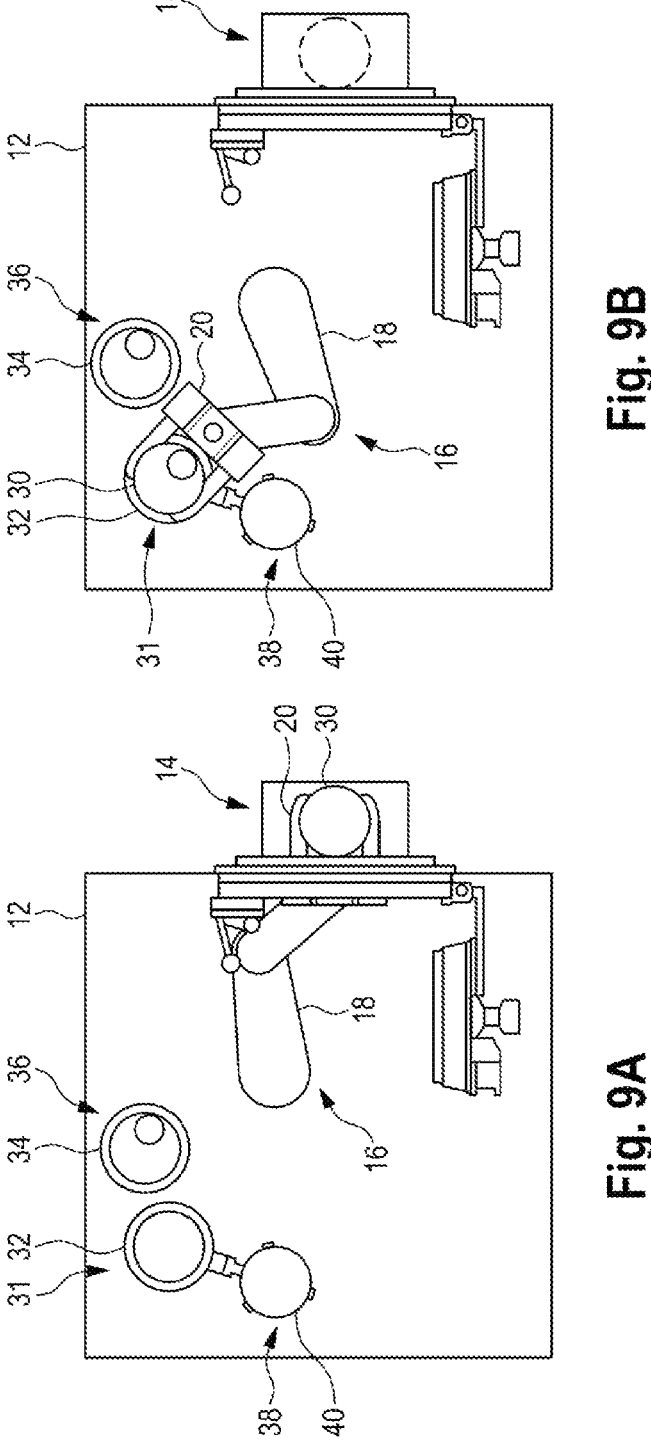
FIG. 9A shows a plan view of the system from FIG. 4 when the nutrient medium carrier is removed from the transfer lock.
FIG. 9B shows a plan view of the system from FIG. 4 when the nutrient medium carrier is placed on the nutrient medium carrier holder of the microbial monitoring device.

In a further step S67 of the method 200, an individual nutrient medium carrier 30 of the at least one nutrient medium carrier 30 is removed from the transfer lock 14 with robot assistance. For this purpose, the robot 16 can be controlled, for example, in such a way that the end effector 20 is moved to the nutrient medium carrier 30 that is to be transferred, and the end effector 20 grips the nutrient medium carrier 30 that is to be transferred. This is shown by way of example in FIG. 9A.

In a further step S68 of method 200, the removed nutrient medium carrier 30 is transferred, with robot assistance, from the transfer lock 14 to a free nutrient medium carrier holder 22 of the at least one nutrient medium carrier holder 22 in the housing 32 of the microbial monitoring device 31. For this purpose, the robot 16 can be controlled, for example, in such a way that the end effector 20 is moved from the transfer lock 14 to the free nutrient medium carrier holder 22.

In a further step S69 of method 200, the transferred nutrient medium carrier 30 is placed, with robot assistance, in the free nutrient medium carrier holder 22 in the housing 32 of the microbial monitoring device 31. The nutrient medium carrier 30 is deposited in particular on a support surface of the nutrient medium carrier holder 22. For this purpose, the robot can be controlled, for example, in such a way that the end effector 20 places the nutrient medium carrier 30, which is to be transferred, on the support surface and releases it. This is shown by way of example in FIG. 9B.

Figure 10B:
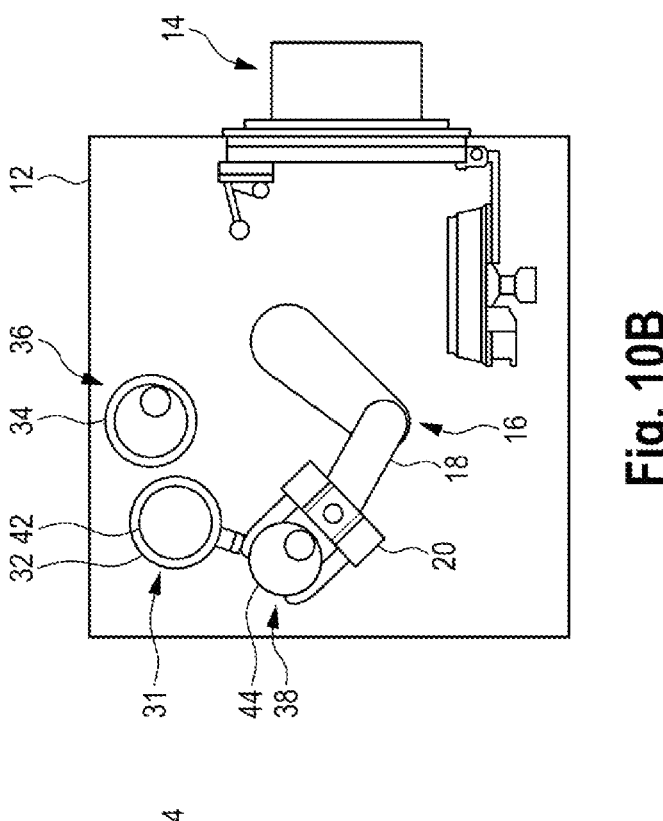
FIG. 10B shows a plan view of the system from FIG. 4 when the lid is deposited on a holder which serves as a lid holder.
Figure 10A:
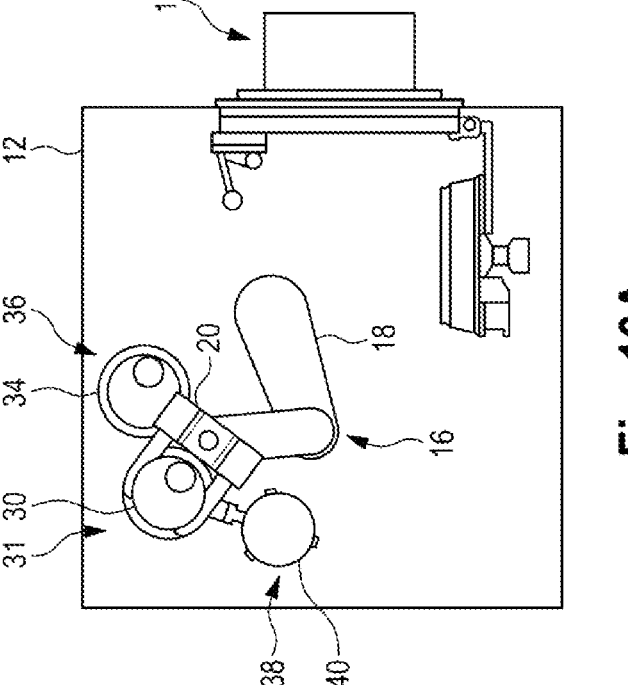
FIG. 10A shows a plan view of the system from FIG. 4 when the lid is removed from the nutrient medium carrier.

In a further step S70 of the method 200, the lid 44 of the transferred nutrient medium carrier 30 is removed from the dish 42 with robot assistance. For this purpose, the robot 16 can be controlled, for example, in such a way that the end effector 18 grips the lid 44 and lifts it. This is shown in FIG. 10A.

In a further step S71 of the method 200, the lid 44 is transferred, with robot assistance, from the nutrient medium carrier holder 22 to a free holder 40 of the storage device 38, the holder 40 serving as a lid holder 24. For this purpose, the robot 16 can be controlled, for example, in such a way that the end effector 18 moves the gripped lid 44 from the nutrient medium carrier holder 22 to the free holder 40.

In a further step S72 of the method 200, the transferred lid 44 is deposited, with robot assistance, on the free holder 40, which serves as a lid holder 24. For this purpose, the robot 16 can be controlled, for example, in such a way that the end effector 18 deposits the transferred lid 44 on the holder 40, in particular sets it down and releases it. This is shown by way of example in FIG. 10B.

If a plurality of nutrient medium carriers 30 are provided in the transfer lock 14, steps S67 to S72 can be repeated for each nutrient medium carrier 30.

Figures 11A, 11B:
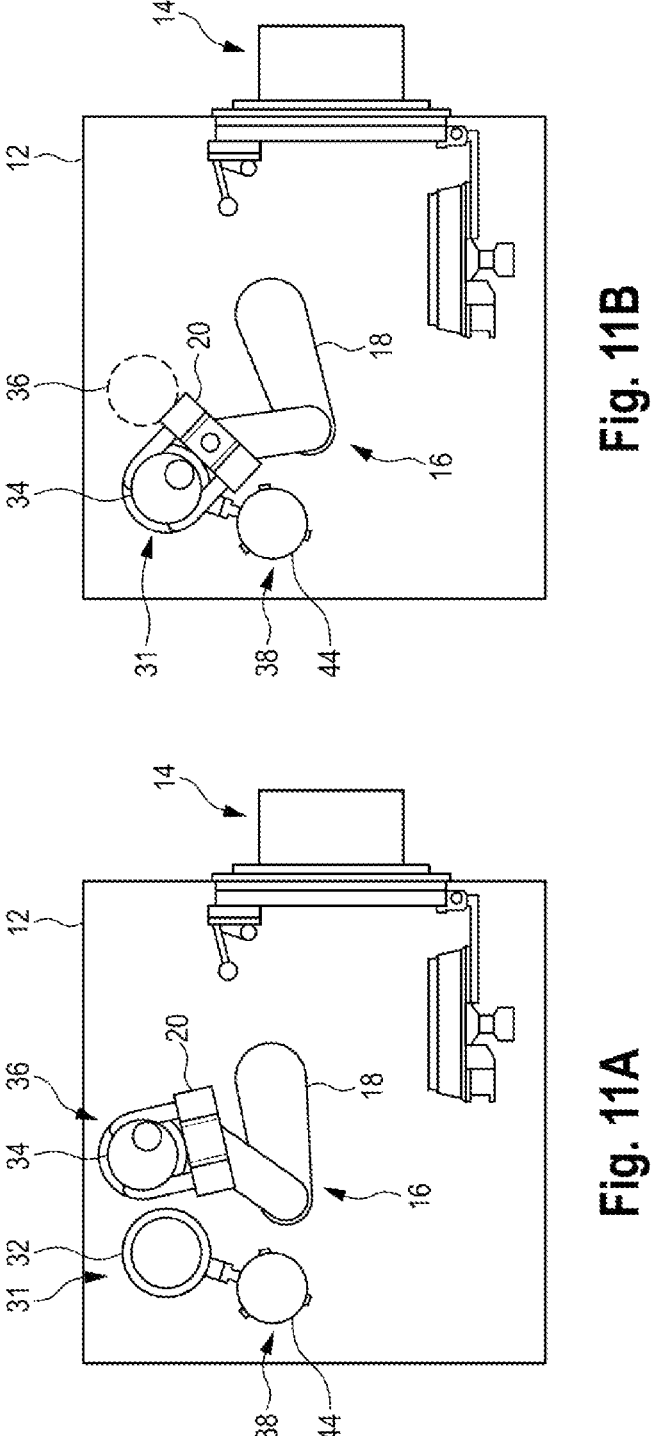
FIG. 11A shows a plan view of the system from FIG. 4 when the housing lid is picked up from the housing lid holder.
FIG. 11B shows a plan view of the system from FIG. 4 when the housing lid is fitted on the housing of the microbial monitoring device.

In a further step S73 of the method 200, the housing lid 34 is picked up from the housing lid holder 36 with robot assistance. For this purpose, the robot 16 can be controlled, for example, in such a way that the end effector 18 grips the housing lid 34 and lifts it. This is shown by way of example in FIG. 11A.

In a further step S74 of the method 200, the housing lid 34 is deposited, with robot assistance, onto the housing 32 of the microbial monitoring device 31. For this purpose, the robot 16 can be controlled, for example, in such a way that the end effector 18 deposits the housing lid 34 on the housing 32 of the microbial monitoring device 31 and releases it. This is shown by way of example in FIG. 11B.

Each dish 42 of the at least one nutrient medium carrier 30 then remains for a predefined period of time in the respective nutrient medium carrier holder 22 in the opened state in the microbial monitoring device, as a result of which the microbial monitoring is carried out in this period of time. The predefined period of time can be 4 hours for example.

In a further step S75 of the method 200, after the transferred nutrient medium carrier 30 has spent the predefined period of time in the corresponding nutrient medium carrier holder 22 of the microbial monitoring device 31, the housing lid 34 is removed, with robot assistance, from the housing 32 of the microbial monitoring device 31. For this purpose, the robot 16 can be controlled, for example, in such a way that the end effector 18 grips the housing lid 34 and lifts it.

In a further step S76 of the method 200, the housing lid 34 is deposited on the housing lid holder 36 with robot assistance. For this purpose, the robot 16 can be controlled, for example, in such a way that the end effector 18 deposits the housing lid 34 on the housing lid holder 36, in particular sets it down and releases it.

In a further step S77 of the method 200, the lid 44 of the nutrient medium carrier 30 is picked up, with robot assistance, from the holder 40, which serves as a lid holder 24. For this purpose, the robot 16 can be controlled, for example, in such a way that the end effector 18 grips the lid 44 and lifts it.

In a further step S78 of the method 200, the lid 44 is transferred, with robot assistance from the holder 40, which serves as lid holder 24, to the nutrient medium carrier holder 22, in the housing 32 of the microbial monitoring device 31, on which the dish 42 of the nutrient medium carrier 30 is arranged. For this purpose, the robot 16 can be controlled, for example, in such a way that the end effector 18 moves the gripped lid 44 from the holder 40, which serves as lid holder 24, to the nutrient medium carrier holder 22.

In a further step S79 of the method 200, the lid 44 is placed, with robot assistance, on the dish 42 of the nutrient medium carrier 30. For this purpose, the robot 16 can be controlled, for example, in such a way that the end effector 18 places the lid 44 on the dish 42 and releases it.

In a further step S80 of the method 200, the nutrient medium carrier 30 is removed, with robot assistance, from the nutrient medium carrier holder 22 from the housing 32 of the microbial monitoring device 31. For this purpose, the robot 16 can be controlled, for example, in such a way that the end effector 18 grips the closed nutrient medium carrier 30.

In a further step S81 of the method 200, the removed nutrient medium carrier 30 is transferred, with robot assistance, from the nutrient medium carrier holder 22 in the housing 32 of the microbial monitoring device 31 to the transfer lock 14. For this purpose, the robot 16 can be controlled, for example, in such a way that the end effector 18 moves the nutrient medium carrier 30 from the nutrient medium carrier holder 22 to the transfer lock 14.

In a further step S82 of the method 200, the transferred nutrient medium carrier 30 is placed in the transfer lock 14 with robot assistance. For this purpose, the robot 16 can be controlled, for example, in such a way that the end effector 18 deposits the nutrient medium carrier 30 in the transfer lock 14 and releases it.

If a plurality of nutrient medium carriers 30 are used, steps S77 to S82 can be repeated for each nutrient medium carrier 30.

In a further step S83 of the method 200, the housing lid 34 is deposited on the housing lid holder 36 with robot assistance. For this purpose, the robot 16 can be controlled, for example, in such a way that the end effector 18 grips the housing lid 34 and lifts it.

In a further step S84 of the method 200, the housing lid 34 is deposited, with robot assistance, onto the housing 32 of the microbial monitoring device 31. For this purpose, the robot 16 can be controlled, for example, in such a way that the end effector 18 places the housing lid 34 on the housing 32 of the microbial monitoring device 31 and releases it.

Figure 12A:
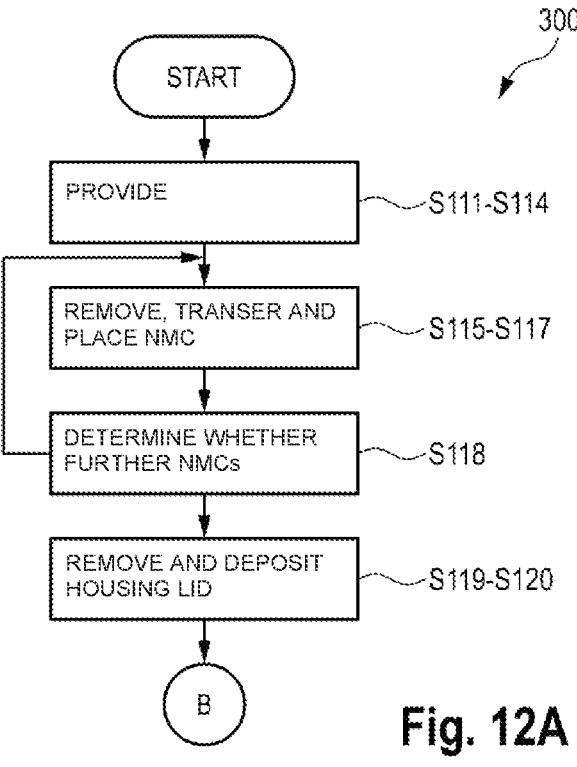
FIGS. 12A, 12B, 12C show schematic representations of a third embodiment of a method for automated microbial monitoring in an isolator.
Figure 12C:
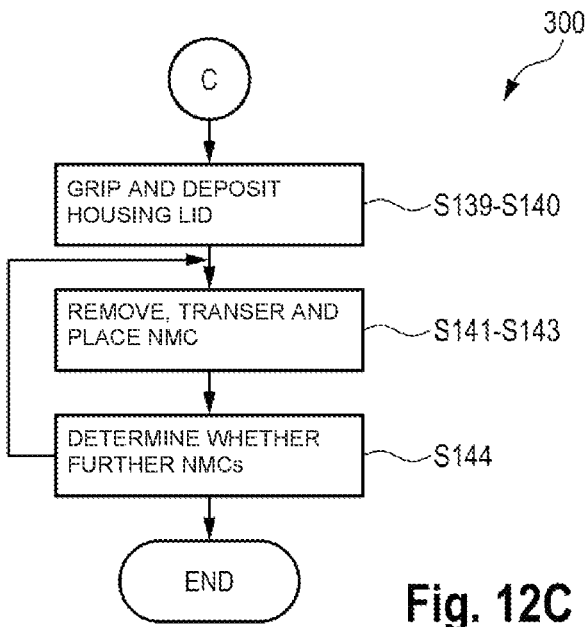
Figure 12B:
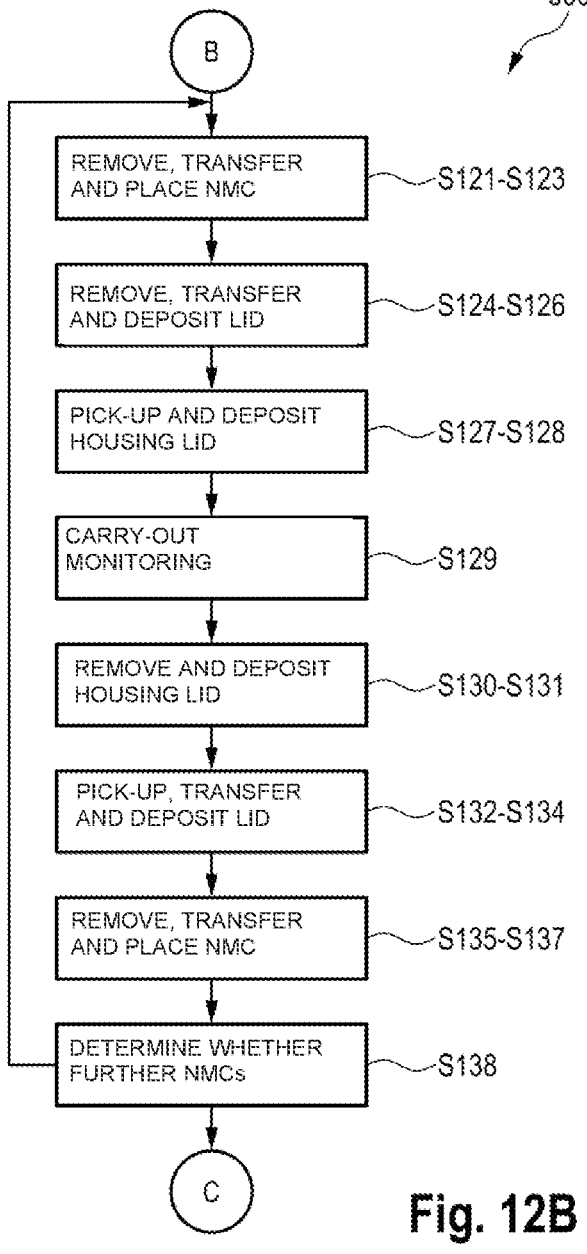

FIGS. 12A, 12B and 12C show a third embodiment of a method 300 for automated microbial monitoring in an isolator 12. The method can, for example, be carried out by means of the system 10 from FIGS. 3 and 4. In particular, the control device 26 can be configured to carry out steps S115 to S144.

Steps S111 to S114 correspond to steps S61 to S64 of the method 200 from FIG. 7.

In a further step S115 of the method 300, an individual nutrient medium carrier 30 of the at least one nutrient medium carrier 30 is removed from the transfer lock 14 with robot assistance. For this purpose, the robot 16 can be controlled, for example, in such a way that the end effector 20 is moved to the nutrient medium carrier 30 that is to be transferred, and the end effector 20 grips the nutrient medium carrier 30 that is to be transferred.

In a further step S116 of the method 300, the removed nutrient medium carrier 30 is transferred, with robot assistance, from the transfer lock 14 to a free holder 40 of the storage device 38, the holder 40 serving as a nutrient medium carrier holder. For this purpose, the robot 16 can be controlled, for example, in such a way that the end effector 20 is moved from the transfer lock 14 to the free holder 40.

In a further step S117 of the method 300, the transferred nutrient medium carrier 30 is placed, with robot assistance, in the free holder 40, which serves as a nutrient medium carrier holder. The nutrient medium carrier 30 is in particular deposited on a support surface of the holder 40. For this purpose, the robot 16 can be controlled, for example, in such a way that the end effector 20 places the nutrient medium carrier 30, which is to be transferred, on the support surface and releases it.

In a further step S118 of the method 300, it is determined whether further nutrient medium carriers 30 are provided in the transfer lock 14. If further nutrient medium carriers 30 are provided in the transfer lock 14, the method 300 goes back to step S115, and steps S115 to S118 are repeated. If no further nutrient medium carriers are provided in the transfer lock 14, the method 300 continues with step S119.

Steps S119 and S120 correspond to steps S65 and S66 of the method 200 from FIG. 7.

In a further step S121 of the method 300, an individual nutrient medium carrier 30 of the at least one nutrient medium carrier 30, which has not yet been inserted in the microbial monitoring device 31 for microbial monitoring, is removed from the respective holder 40 of the storage device 38 with robot assistance. For this purpose, the robot 16 can be controlled, for example, in such a way that the end effector 20 is moved to the nutrient medium carrier 30 that is to be transferred, and the end effector 20 grips the nutrient medium carrier 30 that is to be transferred.

In a further step S122 of the method 300, the removed nutrient medium carrier 30 is transferred, with robot assistance, from the holder 40 of the storage device 38 to the nutrient medium carrier holder 22 in the housing 32 of the microbial monitoring device 31. For this purpose, the robot 16 can be controlled, for example, in such a way that the end effector 20 is moved from the holder 40 to the nutrient medium carrier holder 22.

In a further step S123 of the method 300, the transferred nutrient medium carrier 30 is placed, with robot assistance, in the nutrient medium carrier holder 22 in the housing 32 of the microbial monitoring device 31. The nutrient medium carrier 30 is deposited in particular on a support surface of the nutrient medium carrier holder 22. For this purpose, the robot can be controlled, for example, in such a way that the end effector 20 deposits the nutrient medium carrier 30, which is to be transferred, on the support surface and releases it.

Steps S124 and S128 correspond to steps S70 and S74 of the method 200 from FIG. 7.

In a further step S129 of the method 300, the nutrient medium carrier 30 remains in the opened state for a predefined period of time in the nutrient medium carrier holder 22 of the microbial monitoring device, as a result of which the microbial monitoring is carried out in this period of time. The predefined period of time can be 4 hours, for example.

Steps S130 and S134 correspond to steps S75 and S79 of the method 200 from FIG. 7.

In a further step S135 of the method 300, the nutrient medium carrier 30 is removed, with robot assistance, from the nutrient medium carrier holder 22 from the housing 32 of the microbial monitoring device 31. For this purpose, the robot 16 can be controlled, for example, in such a way that the end effector 18 grips the closed nutrient medium carrier 30.

In a further step S136 of the method 300, the removed nutrient medium carrier 30 is transferred, with robot assistance, from the nutrient medium carrier holder 22 in the housing 32 of the microbial monitoring device 31 to the holder 40 of the storage device 38. For this purpose, the robot 16 can be controlled, for example, in such a way that the end effector 18 moves the nutrient medium carrier 30 from the nutrient medium carrier holder 22 to the transfer lock 14.

In a further step S137 of the method 300, the transferred nutrient medium carrier 30 is placed, with robot assistance, in the holder 40 of the storage device 38. The nutrient medium carrier 30 is deposited in particular on a support surface of the holder 40. For this purpose, the robot 16 can be controlled, for example, in such a way that the end effector 20 places the nutrient medium carrier 30, which is to be transferred, on the support surface and releases it.

In a further step S138 of the method 300, it is determined whether further nutrient medium carriers 30 are still present in the storage device 38 that have not yet been used in the microbial monitoring device 31 for the microbial monitoring. If there are further nutrient medium carriers 30 still present in the storage device 38 that have not yet been used in the microbial monitoring device 31 for microbial monitoring, the method 300 goes back to step S121, and steps S121 to S138 are repeated. If there are no further nutrient medium carriers in the storage device 38 that have not yet been used in the microbial monitoring device 31 for microbial monitoring, the method 300 continues with step S139.

Steps S139 and S140 correspond to steps S83 and S84 of the method 200 from FIG. 7.

In a further step S141 of the method 300, each nutrient medium carrier 30 is removed individually from the respective holder 40 of the storage device 38 with robot assistance. For this purpose, the robot 16 can be controlled, for example, in such a way that the end effector 18 grips the closed nutrient medium carrier 30.

In a further step S142 of the method 300, the removed nutrient medium carrier 30 is transferred, with robot assistance, from the holder 40 of the storage device 38 to the transfer lock 14. For this purpose, the robot 16 can be controlled, for example, in such a way that the end effector 18 moves the nutrient medium carrier 30 from the holder 40 to the transfer lock 14.

In a further step S143 of the method 300, the transferred nutrient medium carrier 30 is placed in the transfer lock 14 with robot assistance. For this purpose, the robot 16 can be controlled, for example, in such a way that the end effector 18 deposits the nutrient medium carrier 30 in the transfer lock 14 and releases it.

In a further step S144 of the method 300, it is determined whether further nutrient medium carriers 30 are arranged in the storage device 38 on a holder 40. If further nutrient medium carriers 30 are arranged in the storage device 38 on a holder 40, the method 300 goes back to step S141, and steps S141 to S143 are repeated. If no further nutrient medium carriers are arranged in the storage device 38 on a holder 40 and therefore all of the nutrient medium carriers are arranged in the transfer lock, the method is ended.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A method for automated microbial monitoring in an isolator, the isolator having a transfer lock, the method comprising the following steps:
  first providing of at least one nutrient medium carrier holder at in each case a first position within the isolator;
  second providing of at least one nutrient medium carrier within the transfer lock;
  first robot-assisted transferring of an individual nutrient medium carrier of the at least one nutrient medium carrier from the transfer lock to a free nutrient medium carrier holder of the at least one nutrient medium carrier holder, wherein the first robot-assisted transferring step transfers the individual nutrient medium carrier one at a time; and
  first robot-assisted placing of the transferred nutrient medium carrier in the free nutrient medium carrier holder.

2. The method as claimed in claim 1, wherein the method comprises, before the step of the first robot-assisted transferring, the following step:
  first robot-assisted removing of the nutrient medium carrier, which is to be transferred, from the transfer lock.

3. The method as claimed in claim 1, wherein each nutrient medium carrier has a dish with nutrient medium and a lid which is placed on an opening of the dish, the method further comprising the following steps:
  third providing of at least one lid holder for storing the lid of the transferred nutrient medium carrier, the at least one lid holder being provided at in each case a second position within the isolator.

4. The method as claimed in claim 3, wherein the method further comprises the following steps:
  robot-assisted removing of the lid from the dish of the transferred nutrient medium carrier;
  second robot-assisted transferring of the lid from the nutrient medium carrier holder to a free lid holder of the at least one lid holder; and
  robot-assisted depositing of the lid on the free lid holder.

5. The method as claimed in claim 4, wherein the method further comprises the following steps, after the transferred nutrient medium carrier has spent a predefined period of time in the corresponding nutrient medium carrier holder:
  robot-assisted picking-up of the lid from the lid holder;
  third robot-assisted transferring of the lid from the lid holder to the corresponding nutrient medium carrier holder; and
  robot-assisted fitting of the lid onto the dish of the nutrient medium carrier.

6. The method as claimed in claim 1, wherein the method further comprises the following steps, after the transferred nutrient medium carrier has spent a predefined period of time in the corresponding nutrient medium carrier holder:
  second robot-assisted removing of the nutrient medium carrier from the nutrient medium carrier holder;

fourth robot-assisted transferring of the nutrient medium carrier from the nutrient medium carrier holder to the transfer lock; and second robot-assisted placing of the nutrient medium carrier in the transfer lock.

7. The method as claimed in claim 1, wherein, in the step of the first providing, a microbial monitoring device with at least one nutrient medium carrier holder is provided.

8. The method as claimed in claim 7, wherein the microbial monitoring device has a housing in which the at least one nutrient medium carrier holder is arranged, the housing having a housing lid, wherein the method further comprises the following steps:

fourth providing of a housing lid holder within the isolator at a third position;

robot-assisted removing of the housing lid; and robot-assisted depositing of the housing lid on the housing lid holder.

9. The method as claimed in claim 7, wherein, in the step of the second providing, a plurality of nutrient medium carriers are provided in the transfer lock, wherein, in the step of the third providing, a storage device with a plurality of holders is provided at the second position, wherein the holders are each able to serve as a nutrient medium carrier holder or lid holder.

10. The method as claimed in claim 9, wherein, in the step of the second providing, the plurality of nutrient medium carriers are provided in a nutrient medium carrier retainer in the transfer lock.

11. The method as claimed in claim 1, wherein, in the step of the second providing, each nutrient medium carrier is provided in a further nutrient medium carrier holder, wherein each further nutrient medium carrier holder is arranged in the transfer lock.

12. The method as claimed in claim 11, wherein each further nutrient medium carrier holder can extend at least partially out of the transfer lock into the isolator, wherein the step of the first robot-assisted transferring takes place in such a way that the respective further nutrient medium carrier holder extends at least partially out of the transfer lock into the isolator and the corresponding nutrient medium carrier is transferred, with robot assistance, from the respective further nutrient medium carrier holder to the free nutrient medium carrier holder within the isolator.

13. The method as claimed in claim 1, wherein a robot is arranged in the isolator, wherein the robot has an end effector for handling a nutrient medium carrier and a support structure for supporting the end effector, wherein the support structure is configured to move the end effector in the isolator, wherein the end effector is configured to grip the nutrient medium carrier.

14. The method as claimed in claim 1, wherein the number of nutrient medium carriers provided in the transfer lock is one to ten nutrient medium carriers.

15. The method as claimed in claim 1, wherein the number of nutrient medium carrier holders provided in the isolator is equal to or greater than the number of nutrient medium carriers provided in the transfer lock.

16. The method as claimed in claim 1, wherein the number of lid holders provided in the isolator is equal to or greater than the number of nutrient medium carriers provided in the transfer lock.

17. A system for automated microbial monitoring in an isolator, wherein the system has the isolator, at least one nutrient medium carrier holder, a robot arranged in the isolator, and a control device, wherein the isolator has a transfer lock, wherein at least one nutrient medium carrier is provided in the transfer lock, wherein the nutrient medium carrier holder is arranged at a first position within the isolator, wherein the robot has an end effector for handling a nutrient medium carrier and a support structure for supporting the end effector, wherein the support structure is configured to move the end effector in the isolator, wherein the end effector is configured to grip the nutrient medium carrier, and wherein the control device is configured to carry out the following steps:

first robot-assisted transferring of in each case an individual nutrient medium carrier of the at least one nutrient medium carrier from the transfer lock to a free nutrient medium carrier holder of the at least one nutrient medium carrier holder, wherein the first robot-assisted transferring step transfers the individual nutrient medium carrier one at a time; and first robot-assisted placing of the transferred nutrient medium carrier in the free nutrient medium carrier holder.

18. The system as claimed in claim 17, wherein the end effector has a receptacle for receiving the nutrient medium carrier, which receptacle is movable between a receiving position, in which the nutrient medium carrier can be received, and a gripping position, in which the nutrient medium carrier can be gripped, wherein each nutrient medium carrier for transferring can be gripped by means of the end effector and moved by means of the robot within the isolator.

19. The system as claimed in claim 17, wherein the system has a microbial monitoring device with at least one nutrient medium carrier holder, wherein the microbial monitoring device has a housing in which at least one nutrient medium carrier holder is arranged, wherein the housing has a housing lid, wherein the housing lid is removable by means of the robot, wherein the system has a housing lid holder for storing the housing lid, wherein the housing lid holder is arranged at a third position within the isolator.

20. The system as claimed in claim 17, wherein each nutrient medium carrier has a dish with nutrient medium and a lid which is placed on an opening of the dish, wherein the lid can be removed by means of the robot, wherein the system furthermore has at least one lid holder for storing the lid, wherein the at least one lid holder is arranged inside the isolator at a second position in each case.

21. A computer program with a program code which is configured, when executed in the control device of a system for automated microbial monitoring in an isolator, wherein the system has the isolator, at least one nutrient medium carrier holder, a robot arranged in the isolator, and the control device, wherein the isolator has a transfer lock, wherein at least one nutrient medium carrier is provided in the transfer lock, wherein the nutrient medium carrier holder is arranged at a first position within the isolator, wherein the robot has an end effector for handling a nutrient medium carrier and a support structure for supporting the end effector, wherein the support structure is configured to move the end effector in the isolator, wherein the end effector is configured to grip the nutrient medium carrier, to carry out the following steps:

first robot-assisted transferring of an individual nutrient medium carrier of the at least one nutrient medium carrier from the transfer lock to a free nutrient medium carrier holder of the at least one nutrient medium carrier holder, wherein the first robot-assisted transferring step transfers the individual nutrient medium carrier one at a time; and first robot-assisted placing of the transferred nutrient medium carrier in the free nutrient medium carrier holder.

\* \* \* \* \*